United States Patent
Clasadonte et al.

(10) Patent No.: US 11,447,459 B2
(45) Date of Patent: *Sep. 20, 2022

(54) USE OF SUBSTITUTED CHROMAN-6-OLS WITH EXTENDED LIPOPHILIC SIDE CHAINS

(71) Applicant: DSM IP ASSETS B.V., Heerlen (NL)

(72) Inventors: Laure Clasadonte, Kaiseraugst (CH); André Duesterloh, Kaiseraugst (CH); Weerasinghe Indrasena, Kaiseraugst (CH); Thomas Netscher, Kaiseraugst (CH); René Stemmler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/041,910

(22) PCT Filed: Mar. 29, 2019

(86) PCT No.: PCT/EP2019/058117
§ 371 (c)(1),
(2) Date: Sep. 25, 2020

(87) PCT Pub. No.: WO2019/185938
PCT Pub. Date: Oct. 3, 2019

(65) Prior Publication Data
US 2021/0130314 A1    May 6, 2021

(30) Foreign Application Priority Data
Mar. 29, 2018 (EP) ..................... 18164860

(51) Int. Cl.
*C07D 311/72* (2006.01)
(52) U.S. Cl.
CPC .................. *C07D 311/72* (2013.01)
(58) Field of Classification Search
CPC .................................................. C07D 311/72
See application file for complete search history.

(56) References Cited

U.S. PATENT DOCUMENTS

| 6,066,745 A | 5/2000 | Baak et al. |
| 7,732,170 B2 | 6/2010 | Bailey et al. |

FOREIGN PATENT DOCUMENTS

| KR | 10-2015-0142152 | 12/2015 |
| WO | 91/07498 | 5/1991 |
| WO | 94/08467 | 4/1994 |
| WO | 97/36996 | 10/1997 |
| WO | 97/37032 | 10/1997 |
| WO | 01/54510 | 8/2001 |
| WO | 03/101950 | 12/2003 |
| WO | 2011/153353 | 12/2011 |
| WO | 2019/185894 | 10/2019 |
| WO | 2019/185898 | 10/2019 |
| WO | 2019/185940 | 10/2019 |

OTHER PUBLICATIONS

Tres et al (2013): STN International CAPLUS database, (Columbus, Ohio), Accession No. 2013: 184424.*

(Continued)

*Primary Examiner* — Golam M Shameem
(74) *Attorney, Agent, or Firm* — Nixon & Vanderhye P.C.

(57) ABSTRACT

The present invention is directed towards the use of substituted chroman-6-ols with extended lipophilic side chains of formula (I) wherein one of the two substituents $R^1$ and $R^2$ is $C_{12-21}$-alkyl and the other of the two substituents $R^1$ and $R^2$ is either hydrogen or $C_{1-5}$-alkyl or $(CH_2)_n$—OH with n being an integer from 1 to 5, and wherein A is $CH(R^3)$, wherein $R^3$, $R^4$ and $R^6$ are independently from each other H or $C_{1-4}$-alkyl, and wherein $R^5$ is H or OH or $C_{1-4}$-alkyl or $C_{1-4}$-alkoxy; with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl, as antioxidants, especially in feed such as pet food and feed ingredients such as fish meal, insect meal and poultry meal, as well as PUFA-containing oil such as marine oil, microbial oil, fungal oil, algal oil and PUFA-containing plant oil. The present invention is further directed towards feed ingredients and feed for insects, aquatic and terrestrial animals comprising such substituted chroman-6-ols with extended lipophilic side chains of formula (I).

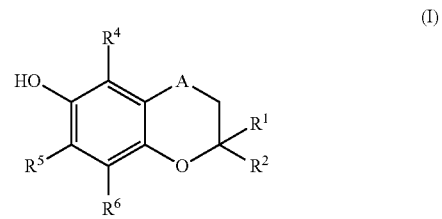

16 Claims, 1 Drawing Sheet

(56) References Cited

OTHER PUBLICATIONS

International Search Report for PCT/EP2019/058117 dated Oct. 9, 2019, 6 pages.
Written Opinion of the ISA for PCT/EP2019/058117 dated Oct. 9, 2019, 7 pages.
Tres et al., "Impact of the oxidative quality of fish oils in feeds on the composition and oxidative stability of chicken and rabbit meat", Animal Feed Science and Technology, 2014, vol. 196, XP002790996, pp. 76-87, (12 total pages).
Lachman et al., "Towards complex utilisation of winemaking residues: Characterisation of grape seeds by total phenols, tocols and essential elements content as a by-product of winemaking", Industrial Crops and Products, 2013, vol. 49, XP002790997, pp. 445-453 (9 total pages).
Morales et al., "Non-fermented and fermented jabuticaba (*Myrciaria cauliflora*Mart.) pomaces as valuable sources of functional ingredients", Food Chemistry, Apr. 6, 2016, vol. 208, XP029527356, pp. 220-227.
Alamgir, "Vitamins, nutraceuticals, food, additives, enzymes, anesthetic acids and comsetics", Therapeutic Use of Medicinal Plants and their Extracts: vol. 2, Progress in Drug Research, Jan. 1, 2018, vol. 74, XP009512903 128 total pages).
Netscher, "Synthesis of Vitamin E," Vitamins and Hormones, vol. 76, 2007, Elsevier Inc., pp. 155-202.

* cited by examiner

USE OF SUBSTITUTED CHROMAN-6-OLS WITH EXTENDED LIPOPHILIC SIDE CHAINS

CROSS-REFERENCE TO RELATED APPLICATIONS

This application is the U.S. national phase of International Application No. PCT/EP2019/058117 filed Mar. 29, 2019 which designated the U.S. and claims priority to EP Application No. 18164860.1 filed Mar. 29, 2018, the entire contents of each of which are hereby incorporated by reference.

SUMMARY

The present invention is directed towards the use of a compound of formula (I) as antioxidant,

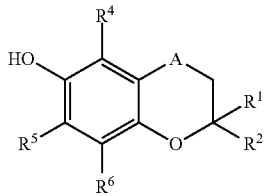

(I)

wherein one of the two substituents $R^1$ and $R^2$ is $C_{12-21}$-alkyl and the other of the two substituents $R^1$ and $R^2$ is either hydrogen or $C_{1-5}$-alkyl or $(CH_2)_n$—OH with n being an integer from 1 to 5, and
wherein A is $CH(R^3)$, and
wherein $R^3$, $R^4$ and $R^6$ are independently from each other H or $C_{1-4}$-alkyl, and
wherein $R^5$ is H or OH or $C_{1-4}$-alkyl or $C_{1-4}$-alkoxy;
with the proviso that at least two of $R^4$, $R^5$ and $R^6$ are not methyl, when $R^3$ is H, and one of the substituents $R^1$ and $R^2$ is methyl and the other of the two substituents $R^1$ and $R^2$ is $C_{12-21}$-alkyl.

With said proviso compounds of formula (I) with at least two of $R^4$, $R^5$ and $R^6$ being methyl, $R^3$ being H and one of the two substituents $R^1$ and $R^2$ being methyl and the other of the two substituents $R^1$ and $R^2$ being $C_{12-21}$-alkyl are not encompassed by formula (I). Thus, if one of the two substituents $R^1$ and $R^2$ is methyl and the other of the two substituents $R^1$ and $R^2$ is 4,8,12-trimethyltridecyl, the compound is selected from alpha-tocopherol, beta-tocopherol and gamma-tocopherol, and thus, not encompassed by formula (I).

The compounds of the present invention are efficient as antioxidants, preferably in feed and feed ingredients. The compounds of the present invention are especially efficient as antioxidants in feed comprising proteins and/or unsaturated fatty acid (derivative)s and in feed ingredients comprising proteins and/or unsaturated fatty acid (derivative)s. "Derivatives" are e.g. the monoglycerides, diglycerides and triglycerides as well as $C_{1-6}$-alkyl esters such as the methyl and ethyl esters.

Compounds of formula (I) with at least two of $R^4$, $R^5$ and $R^6$ being methyl, $R^3$ being H and one of the two substituents $R^1$ and $R^2$ being methyl and the other of the two substituents $R^1$ and $R^2$ being $C_{12-21}$-alkyl may, however, still be present as additional antioxidants in the feed and feed ingredients of the present invention. Thus, if at least two of $R^4$, $R^5$ and $R^6$ are methyl, $R^3$ is H, and one of the two substituents $R^1$ and $R^2$ is methyl and the other of the two substituents $R^1$ and $R^2$ is 4,8,12-trimethyltridecyl, the compound is selected from alpha-tocopherol, beta-tocopherol and gamma-tocopherol, and these compounds may still be present as additional antioxidants in the feed and feed ingredients of the present invention.

BACKGROUND OF THE INVENTION

Unmodified fish meal can spontaneously combust from heat generated by oxidation of the polyunsaturated fatty acids in the fish meal. In the past, factory ships have sunk because of such fires. Strict rules regarding the safe transport of fish meal have been put in place by authorities and the International Maritime Organization (IMO). According to IMO, fishmeal must be stabilized with antioxidants to prevent spontaneous combustion during overseas transport and storage.

The shipping regulations of the United Nations for the Transport of Dangerous Goods (UN-TDG) currently only allow ethoxyquin and BHT as antioxidants to stabilize fish meal for marine transport. But authorization of ethoxyquin has now been suspended in the European Union due to safety and health concerns.

BHT must be added in higher quantities to achieve the same efficacy as ethoxyquin. Furthermore, BHT is currently under safety evaluation by ECHA and its re-registration as feed additive is pending in Europe.

Therefore, there is a need to replace ethoxyquin and BHT as an antioxidant.

DETAILED DESCRIPTION OF THE INVENTION

Figure 1:
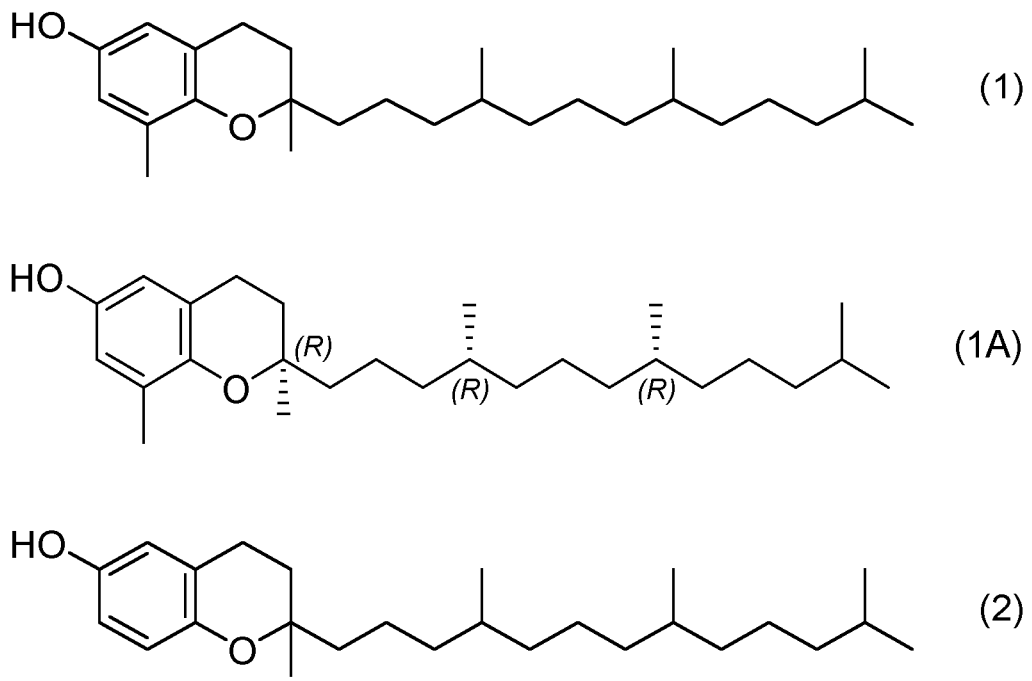
FIG. 1 depicts especially preferred compounds shown by formulas (1) and (2) whereby all possible diastereomers and enantiomers are included as well as a preferred enantiomer compound shown by formula (1A)

This need is fulfilled by the present invention, which is directed to the use of a compound of formula (I) as antioxidant,

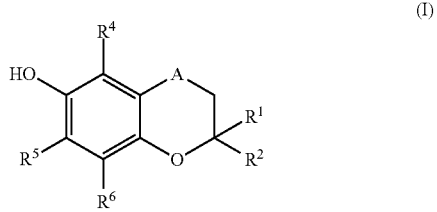

(I)

wherein one of the two substituents $R^1$ and $R^2$ is $C_{12-21}$-alkyl and the other of the two substituents $R^1$ and $R^2$ is either hydrogen or $C_{1-5}$-alkyl or $(CH_2)_n$—OH
with n being an integer from 1 to 5, and
wherein A is $CH(R^3)$, and
wherein $R^3$, $R^4$ and $R^6$ are independently from each other H or $C_{1-4}$-alkyl, and wherein $R^5$ is H or OH or $C_{1-4}$-alkyl or $C_{1-4}$-alkoxy; with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl;

and with the preferences for the substituents $R^1$ to $R^6$ as given below.

The compounds of formula (I) with the preferences as given below are not only suitable for stabilizing fish meal, but they are also suitable for stabilizing feed ingredients and feed. Preferences for feed ingredients and feed are given below.

Compounds of Formula (I)

"alkyl" and "alkoxy" in the context of the present invention encompass linear alkyl and branched alkyl, and linear alkoxy and branched alkoxy, respectively.

In a preferred embodiment of the present invention in compound of formula (I) one of the two substituents $R^1$ and $R^2$ is $C_{12-21}$-alkyl, preferably one of the two substituents $R^1$ and $R^2$ is linear or branched $C_{15-20}$-alkyl, more preferably one of the two substituents $R^1$ and $R^2$ is linear or branched $C_{16-18}$-alkyl, most preferably one of the two substituents $R^1$ and $R^2$ is 4,8,12-trimethyltridecyl, and the other of the two substituents $R^1$ and $R^2$ is either hydrogen or $C_{1-5}$-alkyl, and $R^3$, $R^4$ and $R^6$ are independently from each other H or $C_{1-4}$-alkyl, and
$R^5$ is H or OH or $C_{1-4}$-alkyl or $C_{1-4}$-alkoxy;
with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl.

More preferably in compound of formula (I) one of the two substituents $R^1$ and $R^2$ is $C_{12-21}$-alkyl, preferably one of the two substituents $R^1$ and $R^2$ is linear or branched $C_{15-20}$-alkyl, more preferably one of the two substituents $R^1$ and $R^2$ is linear or branched $C_{16-18}$-alkyl, most preferably one of the two substituents $R^1$ and $R^2$ is 4,8,12-trimethyltridecyl, and the other of the two substituents $R^1$ and $R^2$ is either hydrogen or methyl or ethyl, and
$R^3$ and $R^4$ are independently from each other H or methyl or ethyl, and
$R^6$ is H or $C_{1-4}$-alkyl, preferably $R^6$ is H or methyl or ethyl, and
$R^5$ is H or OH or methyl or ethyl or methoxy or ethoxy;
with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl.

Even more preferably in compound of formula (I) one of the two substituents $R^1$ and $R^2$ is $C_{12-21}$-alkyl, preferably one of the two substituents $R^1$ and $R^2$ is linear or branched $C_{15-20}$-alkyl, more preferably one of the two substituents $R^1$ and $R^2$ is linear or branched $C_{16-18}$-alkyl, most preferably one of the two substituents $R^1$ and $R^2$ is 4,8,12-trimethyltridecyl, and the other of the two substituents $R^1$ and $R^2$ is either hydrogen or methyl, and
$R^3$ is H, and
$R^4$ is H or methyl, and
$R^6$ is H or $C_{1-4}$-alkyl, preferably $R^6$ is H or methyl or ethyl, and
$R^5$ is H or OH or methyl or methoxy; with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl.

Furthermore, preferably in compound of formula (I) one of the two substituents $R^1$ and $R^2$ is $C_{12-21}$-alkyl, preferably one of the two substituents $R^1$ and $R^2$ is linear or branched $C_{15-20}$-alkyl, more preferably one of the two substituents $R^1$ and $R^2$ is linear or branched $C_{16-18}$-alkyl, most preferably one of the two substituents $R^1$ and $R^2$ is 4,8,12-trimethyltridecyl, and the other of the two substituents $R^1$ and $R^2$ is methyl, and
$R^3$ is H, and $R^4$ and $R^5$ are independently from each other H or methyl, $R^6$ is H or $C_{1-4}$-alkyl, preferably $R^6$ is H or methyl or ethyl; and
with the proviso that at least one of $R^4$, $R^5$ and $R^6$ is H.

Furthermore, more preferably in compound of formula (I) one of the two substituents $R^1$ and $R^2$ is $C_{12-21}$-alkyl, preferably one of the two substituents $R^1$ and $R^2$ is linear or branched $C_{15-20}$-alkyl, more preferably one of the two substituents $R^1$ and $R^2$ is linear or branched $C_{16-18}$-alkyl, most preferably one of the two substituents $R^1$ and $R^2$ is 4,8,12-trimethyltridecyl, and the other of the two substituents $R^1$ and $R^2$ is methyl, and
$R^3$ and $R^4$ are H, and $R^5$ is H or methyl, and $R^6$ is H or $C_{1-4}$-alkyl, preferably $R^6$ is H or methyl or ethyl.

Most preferably in compound of formula (I) one of the two substituents $R^1$ and $R^2$ is $C_{12-21}$-alkyl, preferably one of the two substituents $R^1$ and $R^2$ is linear or branched $C_{15-20}$-alkyl, more preferably one of the two substituents $R^1$ and $R^2$ is linear or branched $C_{16-18}$-alkyl, most preferably one of the two substituents $R^1$ and $R^2$ is 4,8,12-trimethyltridecyl, and the other of the two substituents $R^1$ and $R^2$ is methyl, and
$R^3$, $R^4$ and $R^5$ are H, and $R^6$ is H or $C_{1-4}$-alkyl, preferably $R^6$ is H or methyl, more preferably $R^6$ is methyl.

Especially preferred are the following compounds of formulae (1) and (2), whereby all possible diastereomers and enantiomers are included, meaning that also all possible isomers having any configuration at the chiral centers (marked with asterisks *) are included,

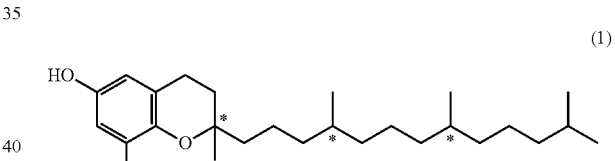

(1)

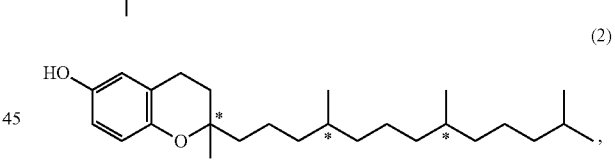

(2)

as well as the enantiomer of formula (1A), (2R,4'R,8'R)-delta-tocopherol ((R)-2,8-dimethyl-2-((4R,8R)-4,8,12-trimethyltridecyl)chroman-6-ol),

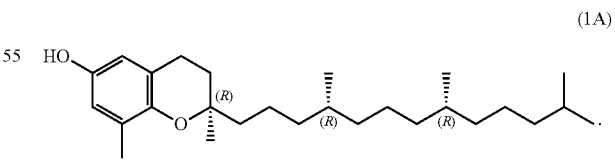

(1A)

Most preferred is the compound of formula (1A).

Use as Antioxidants, Feed and Feed Ingredients

The compounds of the present invention are efficient as antioxidants, preferably in feed and feed ingredients.

Non-limiting examples of feed are pet food, feed for aquatic animals, feed for terrestrial animals such as poultry and pigs, and feed for insects.

Non-limiting examples of feed ingredients are poultry meal, fish meal, insect meal and PUFA-containing oil.

"PUFA(s)" means polyunsaturated fatty acid(s) such as docosahexaenoic acid ("DHA") and/or eicosapentaenoic acid ("EPA") and/or docosapentaenoic acid ("DPA") and/or oleic acid and/or stearidonic acid and/or linoleic acid and/or alpha-linolenic acid ("ALA") and/or gamma-linolenic acid and/or arachidonic acid ("ARA") and/or the esters of all of them, whereby the term "esters" encompasses monoglycerides, diglycerides and triglycerides as well as $C_{1-6}$-alkyl esters such as especially the methyl esters and the ethyl esters, whereby the triglycerides are often dominant.

DHA, EPA, ALA and stearidonic acid are omega-3 fatty acids, whereas linoleic acid, gamma-linolenic acid and ARA are omega-6 fatty acids.

The term "DPA" encompasses two isomers, the omega-3 fatty acid clupanodonic acid (7Z,10Z,13Z,16Z,19Z-docosapentaenoic acid) and the omega-6 fatty acid osbond acid (4Z,7Z,10Z,13Z,16Z-docosapentaenoic acid).

In accordance with the invention, the polyunsaturated fatty acid (PUFA) is preferably DHA and/or EPA and/or DPA and/or any ester thereof, more preferably the polyunsaturated fatty acid (PUFA) is preferably DHA and/or EPA and/or any ester thereof.

Examples of PUFA-containing oils are marine oil, such as preferably fish oil, microbial biomass containing polyunsaturated fatty acids and/or their esters ("microbial oil"), preferably containing high amounts of docosahexaenoic acid ("DHA") and/or eicosapentaenoic acid ("EPA") and/or docosapentaenoic acid ("DPA") and/or their esters, and oil containing high amounts of PUFAs and/or their esters, preferably containing high amounts of docosahexaenoic acid ("DHA") and/or eicosapentaenoic acid ("EPA") and/or docosapentaenoic acid ("DPA") and/or their esters, extracted from microbial biomass, such as fungae ("fungal oil") or algae ("algal oil"), and plant oil with relatively high amounts of PUFAs and/or their esters, ("PUFA-containing plant oil"), such as e.g. canola seed oil, linseed/flaxseed oil, hempseed oil, pumpkin seed oil, evening primrose oil, borage seed oil, blackcurrent seed oil, sallow thorn/sea buckthorn oil, chia seed oil, argan oil and walnut oil.

Further Objects of the Present Invention

Thus, in addition, the present invention is
(1) directed to the use of the compounds of formula (I) as antioxidants in feed, such as especially feed for aquatic animals, feed for terrestrial animals such as poultry, pigs and pets, and feed for insects; as well as
(2) directed to the use of the compounds of formula (I) as antioxidants in feed ingredients, such as especially poultry meal, fish meal, insect meal and PUFA-containing oil, and
(3) directed to feed, such as especially feed for aquatic animals, feed for terrestrial animals such as poultry, pigs and pets, and feed for insects, comprising such compounds of formula (I) and
(4) directed to feed ingredients, such as especially poultry meal, fish meal, insect meal and PUFA enriched oil, comprising such compounds of formula (I).

Thus, the present invention is directed to feed for aquatic animals comprising such compounds of formula (I) with the preferences as given above.

The present invention is also directed to feed for insects and terrestrial animals, e.g. pigs, poultry and pets, comprising such compounds of formula (I) with the preferences as given above.

Aquatic animals in the context of the present invention encompass farmed crustacea such as shrimp and carnivorous species of farmed fish such as salmons, rainbow trout, brown trout (*Salmo trutta*) and gilthead seabream.

Thus, the feed for aquatic animals comprising the compounds of formula (I) are especially fed to the aquatic animals as cited above.

I. Feed Ingredients

Feed ingredients are broadly classified into cereal grains, protein meals, fats and oils, minerals, feed additives, and miscellaneous raw materials, such as roots and tubers.

Further Antioxidants

The compounds of formula (I) can be used in combination with one or more other antioxidants as described below.

In an embodiment of the present invention the feed ingredients of the present invention additionally comprise a mixture of 2-tert-butyl-4-methoxyphenol and 3-tert-butyl-4-methoxyphenol, which is known under the name "BHA" (butylated hydroxyanisole).

In a further embodiment of the present invention the feed ingredients of the present invention additionally comprise ascorbyl palmitate.

In another embodiment of the present invention the feed ingredients of the present invention additionally comprise BHA and ascorbyl palmitate.

Instead of ascorbyl palmitate other esters of ascorbic acid such as the esters of ascorbic acid with linear $C_{12-20}$ alkanols, preferably the esters of ascorbic acid with linear $C_{14-18}$ alkanols, may also be used, so that further embodiments of the present invention are directed to feed ingredients that additionally comprise esters of ascorbic acid with linear $C_{12-20}$ alkanols, preferably esters of ascorbic acid with linear $C_{14-18}$ alkanols, more preferably ascorbyl palmitate, whereby optionally BHA may also be present.

The feed ingredients may also comprise additionally alpha-tocopherol and/or gamma-tocopherol, whereby either an ester of ascorbic acid with a linear $C_{12-20}$ alkanol with the preferences as given above or BHA or both may additionally be present.

The feed ingredients themselves are described in more detail below.

1. PUFA-Containing Oils

In the context of the present invention the term "PUFA-containing oil" encompasses marine oil, such as especially fish oil, microbial biomass containing polyunsaturated fatty acids ("PUFAs"), especially docosahexaenoic acid ("DHA") and/or eicosapentaenoic acid ("EPA") and/or docosapentaenoic acid ("DPA") and/or their esters ("microbial oil");

oil containing high amounts of PUFAs, especially containing high amounts of DHA and/or EPA and/or DPA and/or their esters extracted from microbial biomass as e.g., fungi ("fungal oil") or algae ("algal oil");

Plant oil with high amounts of PUFAs and/or their esters ("PUFA-containing plant oil"), such as e.g. canola seed oil, linseed/flaxseed oil, hempseed oil, pumpkin seed oil, evening primrose oil, borage seed oil, blackcurrent seed oil, sallow thorn/sea buckthorn oil, chia seed oil, argan oil and walnut oil.

The term "DHA" does not only encompass the acid but also derivatives thereof such as monoglycerides, diglycerides and triglycerides as well as $C_{1-6}$-alkyl esters such as the methyl and ethyl esters. The same applies for "EPA" and "DPA" and all the other PUFAs.

Fish oil and algal oil are common feed ingredients. Instead of fish oil and algal oil also the other PUFA-containing oils named above may be used as feed ingredients, i.e.:

microbial biomass containing PUFAs ("microbial oil")

oil containing high amounts of PUFAs extracted from microbial biomass, such as especially fungal oil, and plant oil with high amounts of PUFAs.

The above-mentioned feed ingredients may not only be used as alternative of fish oil and algal oil, but also in addition.

Examples of PUFA-containing oils that are used as feed ingredients are given below in more detail.

Marine Oil

Examples of suitable marine oils include, but are not limited to, Atlantic fish oil, Pacific fish oil, or Mediterranean fish oil, or any mixture or combination thereof.

In more specific examples, a suitable fish oil can be, but is not limited to, pollack oil, bonito oil, pilchard oil, tilapia oil, tuna oil, sea bass oil, halibut oil, spearfish oil, barracuda oil, cod oil, menhaden oil, sardine oil, anchovy oil, capelin oil, herring oil, mackerel oil, salmonid oil, tuna oil, and shark oil, including any mixture or combination thereof.

Other marine oils suitable for use herein include, but are not limited to, squid oil, cuttle fish oil, octopus oil, krill oil, seal oil, whale oil, and the like, including any mixture or combination thereof.

For stabilizing marine oil an amount of at least one compound of formula (I) ranging from 10 to 500 ppm, preferably ranging from 30 to 300 ppm, more preferably ranging from 100 to 250 ppm, based on the total amount of the marine oil, is usually sufficient. The same applies for the other PUFA-containing oils such as microbial oil, algal oil, fungal oil and PUFA-containing plant oil.

A commercially available example of marine oil is the fish oil "MEG-3" (Bleached 30S TG Fish oil) from DSM Nutritional Products, LLC (US) whose specification and composition is shown in Tables I and II below:

TABLE I

| ANALYSIS | SPECIFICATIONS |
|---|---|
| Colour | Max. 6 Gardner Colour |
| Free Fatty Acid (as % Oleic) | Max. 0.4% |
| p-Anisidine Value | Max. 12 (at time of release) |
| Peroxide Value | Max. 3 milli equivalents/kg (at time of release) |
| % Moisture | Max. 0.05% |
| Cold Test | Remains clear at 0° C. for 3 hours |
| Cholesterol | Report Actual |
| TOTOX ((2 × Peroxide Value) + (p-Anisidine Value)) | Max. 20 |

The peroxide value is defined as the amount of peroxide oxygen per 1 kilogram of oil. Traditionally this is expressed in units of milliequivalents or meq/kg.

Winterization is part of the processing of fish oil, and it is performed to remove solid fat in the oil. The "cold test" is performed to check if any solid fat is present and precipitated in the oil when cooled to 0° C. within a specific period of time. In this fish oil (Product Code: FG30TG), any such precipitation is checked for 3 hours at 0° C.

TABLE II

| Fatty Acid Profile | |
|---|---|
| EPA (A %) | Min. 18 |
| EPA mg/g (as TG) | Min. 170 |
| DHA (A %) | Min. 12 |
| DHA mg/g (as TG) | Min. 110 |
| EPA + DHA (A %) | Min. 30 |
| Total Omega 3 (A %) | Min. 34 |

"TG" = triglyceride;
"A %" = "area %" = area percentage by GC based on 24 peak analysis (meaning the 24 highest peaks have been analyzed)

Oil Containing High Amounts of PUFAs, Especially Containing High Amounts of DHA and/or EPA and/or DPA and/or their Esters, Extracted from Microbial Biomass as e.g., Fungi ("Fungal Oil") or Algae ("Algal Oil")

Algal Oil

"Algal oil" is an oil containing high amounts of DHA and/or EPA and/or DPA and/or their esters extracted from algae as microbial source/biomass.

An example of algal oil is the commercially available "Algal oil containing EPA+DPA" from DSM Nutritional Products, LLC (US) whose composition is shown in the Table III below:

TABLE III

| Fatty Acid Profile | |
|---|---|
| DHA + EPA content, mg/g oil | 587 mg/g |
| DHA content, mg/g oil | 401 mg/g |
| EPA content, mg/g oil | 186 mg/g |
| TOTOX ((2 × Peroxide Value) + (p-Anisidine Value)) | 5 |
| Free Fatty Acid | 0.6% |
| Moisture | <0.05% |

A further example of a crude oil containing high amounts of DHA and/or EPA extracted from microbial sources as e.g., algae, is the oil extracted from Algae *Schizochytrium* Biomass, whose specification is given in the following Table IV.

TABLE IV

| Specification | Aqua (Base Product) |
|---|---|
| DHA + EPA, mg/g oil | minimal 500 mg/g |
| DHA content, mg/g oil | minimal 250 mg/g (at least 25% -> 40%) |
| EPA content, mg/g oil | minimal 100 mg/g (at least 10% -> 25%) |
| Minimal ratio EFIA:DHA | 1:4 |
| Maximal ratio EPA:DHA | 1:1 |
| TOTOX ((2 × Peroxide Value) + (p-Anisidine Value)) | maximum 35 |
| Free fatty acid | maximal 5% |
| Moisture | maximal 0.75% |
| DPA n-3 (omega-3 docosapentaenoic acid), % | <6 |
| Arachidonic Acid, % | <2 |
| Stearic, % | <2.5 |
| Palmitic, % | <30 |
| Shelf life | 6 months at 25° C. |
| Total Fat | Record |
| Crude Fat | >92% |

Microbial Biomass Containing Polyunsaturated Fatty Acids ("PUFAs"), Especially Docosahexaenoic Acid and/or Eicosapentaenoic Acid and/or Docosapentaenoic Acid ("DPA") and/or their Esters The biomass preferably comprises cells which produce PUFAs hetero-trophically. According to the invention, the cells are preferably selected from algae, fungi, particularly yeasts, bacteria, or protists. The cells are more preferably microbial algae or fungi.

Suitable cells of oil-producing yeasts are, in particular, strains of *Yarrowia, Candida, Rhodotorula, Rhodosporidium, Cryptococcus, Trichosporon* and *Lipomyces*.

Oil produced by a microorganism or obtained from a microbial cell is referred to as "microbial oil". Oil produced by algae and/or fungi is referred to as an algal and/or a fungal oil, respectively.

As used herein, a "microorganism" refers to organisms such as algae, bacteria, fungi, protist, yeast, and combinations thereof, e.g., unicellular organisms. A microorganism includes but is not limited to, golden algae (e.g., microorganisms of the kingdom Stramenopiles); green algae; diatoms; dinoflagellates (e.g., microorganisms of the order Dinophyceae including members of the genus *Crypthecodinium* such as, for example, *Crypthecodinium cohnii* or *C. cohnii*); microalgae of the order Thraustochytriales; yeast (Ascomycetes or Basidiomycetes); and fungi of the genera *Mucor, Mortierella,* including but not limited to *Mortierella alpina* and *Mortierella* sect. *schmuckeri,* and *Pythium,* including but not limited to *Pythium insidiosum*.

In one embodiment, the microorganisms of the kingdom Stramenopiles may in particular be selected from the following groups of microorganisms: Hamatores, Proteromonads, Opalines, Developayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinales, Pedinellales, Dictyochales), Chrysomeridales, Sarcinochrysidales, Hydrurales, Hibberdiales, and Chromulinales.

In one embodiment, the microorganisms are from the genus *Mortierella,* genus *Crypthecodinium,* genus *Thraustochytrium,* and mixtures thereof. In a further embodiment, the microorganisms are from *Crypthecodinium Cohnii*. In a further embodiment, the microorganisms are from *Mortierella alpina*. In a still further embodiment, the microorganisms are from *Schizochytrium* sp. In yet an even further embodiment, the microorganisms are selected from *Crypthecodinium Cohnii, Mortierella alpina, Schizochytrium* sp., and mixtures thereof.

In a still further embodiment, the microorganisms include, but are not limited to, microorganisms belonging to the genus *Mortierella,* genus *Conidiobolus,* genus *Pythium,* genus *Phytophthora,* genus *Penicillium,* genus *Cladosporium,* genus *Mucor,* genus *Fusarium,* genus *Aspergillus,* genus *Rhodotorula,* genus *Entomophthora,* genus *Echinosporangium,* and genus *Saprolegnia*.

In an even further embodiment, the microorganisms are from microalgae of the order Thraustochytriales, which includes, but is not limited to, the genera *Thraustochytrium* (species include *arudimentale, aureum, benthicola, globosum, kinnei, motivum, multirudimentale, pachydermum, proliferum, roseum, striatum*); the genera *Schizochytrium* (species include *aggregatum, limnaceum, mangrovei, minutum, octosporum*); the genera *Ulkenia* (species include *amoeboidea, kerguelensis, minuta, profunda, radiate, sailens, sarkariana, schizochytrops, visurgensis, yorkensis*); the genera *Aurantiacochytrium;* the genera *Oblongichytrium;* the genera *Sicyoidochytium;* the genera *Parientichytrium;* the genera *Botryochytrium;* and combinations thereof. Species described within *Ulkenia* will be considered to be members of the genus *Schizochytrium*. In another embodiment, the microorganisms are from the order Thraustochytriales. In yet another embodiment, the microorganisms are from *Thraustochytrium*. In still a further embodiment, the microorganisms are from *Schizochytrium* sp.

In certain embodiments, the oil can comprise a marine oil. Examples of suitable marine oils are the ones as given above.

The biomass according to the invention preferably comprises cells, and preferably consists essentially of such cells, of the taxon Labyrinthulomycetes (Labyrinthulea, net slime fungi, slime nets), in particular, those from the family of Thraustochytriaceae. The family of the Thraustochytriaceae (Thraustochytrids) includes the genera *Althomia, Aplanochytrium, Aurantiochytrium, Botryochytrium, Elnia, Japonochytrium, Oblongichytrium, Parietichytrium, Schizochytrium, Sicyoidochytrium, Thraustochytrium,* and *Ulkenia*. The biomass particularly preferably comprises cells from the genera *Aurantiochytrium, Oblongichytrium, Schizochytrium,* or *Thraustochytrium,* more preferably from the genus *Schizochytrium*.

In accordance with the invention, the polyunsaturated fatty acid (PUFA) is preferably DHA and/or EPA and/or their esters as defined above.

The cells present in the biomass are preferably distinguished by the fact that they contain at least 20 weight-%, preferably at least 30 weight-%, in particular at least 35 weight-%, of PUFAs, in each case based on cell dry matter.

In a very preferred embodiment of the current invention, cells, in particular a *Schizochytrium* strain, is employed which produces a significant amount of EPA and DHA, simultaneously, wherein DHA is preferably produced in an amount of at least 20 weight-%, preferably in an amount of at least 30 weight-%, in particular in an amount of 30 to 50 weight-%, and EPA is produced in an amount of at least 5 weight-%, preferably in an amount of at least 10 weight-%, in particular in an amount of 10 to 20 weight-% (in relation to the total amount of lipid as contained in the cells, respectively).

Preferred species of microorganisms of the genus *Schizochytrium,* which produce EPA and DHA simultaneously in significant amounts, as mentioned before, are deposited under ATCC Accession No. PTA-10208, PTA-10209, PTA-10210, or PTA-10211, PTA-10212, PTA-10213, PTA-10214, PTA-10215.

DHA and EPA producing *Schizochytrium* strains can be obtained by consecutive mutagenesis followed by suitable selection of mutant strains which demonstrate superior EPA and DHA production and a specific EPA:DHA ratio. Any chemical or nonchemical (e.g. ultraviolet (UV) radiation) agent capable of inducing genetic change to the yeast cell can be used as the mutagen. These agents can be used alone or in combination with one another, and the chemical agents can be used neat or with a solvent.

Methods for producing the biomass, in particular, a biomass which comprises cells containing lipids, in particular PUFAs, particularly of the order Thraustochytriales, are described in detail in the prior art (see e.g. WO 91/07498, WO 94/08467, WO 97/37032, WO 97/36996, WO 01/54510). As a rule, the production takes place by cells being cultured in a fermenter in the presence of a carbon source and a nitrogen source, along with a number of additional substances like minerals that allow growth of the microorganisms and production of the PUFAs. In this context, biomass densities of more than 100 grams per litre and production rates of more than 0.5 gram of lipid per litre per hour may be attained. The process is preferably carried out in what is known as a fed-batch process, i.e. the carbon and nitrogen sources are fed in incrementally during the fermentation. When the desired biomass has been obtained, lipid production may be induced by various measures, for example by limiting the nitrogen source, the carbon source or the oxygen content or combinations of these.

In a preferred embodiment of the current invention, the cells are grown until they reach a biomass density of at least 80 or 100 g/l, more preferably at least 120 or 140 g/l, in particular at least 160 or 180 g/l (calculated as dry-matter content). Such processes are for example disclosed in U.S. Pat. No. 7,732,170.

Preferably, the cells are fermented in a medium with low salinity, in particular, so as to avoid corrosion. This can be achieved by using chlorine-free sodium salts as the sodium source instead of sodium chloride, such as, for example, sodium sulphate, sodium carbonate, sodium hydrogen carbonate or soda ash. Preferably, chloride is used in the fermentation in amounts of less than 3 g/l, in particular, less than 500 mg/l, especially preferably less than 100 mg/l.

PUFA-Containing Plant Oils: Plant Oils with Relatively High Amounts of PUFAs, Especially with High Amounts of DHA and/or EPA Such as e.g., Canola Seed Oil The plant cells may, in particular, be selected from cells of the families Brassicaceae, Elaeagnaceae and Fabaceae. The cells of the family Brassicaceae may be selected from the genus *Brassica*, in particular, from oilseed rape, turnip rape and Indian mustard; the cells of the family Elaeagnaceae may be selected from the genus *Elaeagnus*, in particular, from the species *Oleae europaea*; the cells of the family Fabaceae may be selected from the genus *Glycine*, in particular, from the species *Glycine max*.

EXAMPLES

Canola seed oil with a content of DHA of at least 9% by weight, of at least 12% by weight, of at least 15% by weight, or of at least 20% by weight, based on the total weight of the canola seed oil;

Canola seed oil with a content of EPA of at least 9% by weight, of at least 12% by weight, of at least 15% by weight, or of at least 20% by weight, based on the total weight of the canola seed oil.

Examples of PUFA-containing plant oils containing high amounts of other PUFAs than EPA and/or DHA and/or DPA and/or their esters are linseed/flaxseed oil, hempseed oil, pumpkin seed oil, evening primrose oil, borage seed oil, blackcurrant seed oil, sallow thorn/sea buckthorn oil, chia seed oil, argan oil and walnut oil.

2. Other Feed Ingredients

Poultry Meal/Chicken Meal

Poultry meal is a high-protein commodity used as a feed ingredient. It is made from grinding clean, rendered parts of poultry carcasses and can contain bones, offal, undeveloped eggs, and some feathers. Poultry meal quality and composition can change from one batch to another.

Chicken meal, like poultry meal, is made of "dry, ground, rendered clean parts of the chicken carcass" according to AAFCO and may contain the same ingredients as poultry meal. Chicken meal can vary in quality from batch to batch. Chicken meal costs less than chicken muscle meat and lacks the digestibility of chicken muscle meat.

Poultry meal contains preferably not less than 50 weight-% of crude protein, not less than 5 weight-% of crude fat, not more than 5 weight-% of crude fiber, not more than 40 weight-% of ash and not more than 15 weight-% of water, each based on the total weight of the poultry meal, whereby the total amount of all ingredients sums up to 100 weight-%.

More preferably poultry meal contains from 50 to 85 weight-% of crude protein, and from 5 to 20 weight-% of crude fat, and from 1 to 5 weight-% of crude fiber, and from 5 to 40 weight-% of ash, and from 5 to 15 weight-% of water, each based on the total weight of the poultry meal, whereby the total amount of all ingredients sums up to 100 weight-%.

For stabilizing poultry meal an amount of at least one compound of formula (I) ranging from 10 to 1000 ppm, preferably ranging from 30 to 700 ppm, more preferably ranging from 100 to 500 ppm, based on the total amount of the poultry meal, is usually sufficient.

The same amounts also apply for chicken meal.

Fish Meal

Fish meal contains preferably not less than 50 weight-% of crude protein, and not more than 20 weight-% of crude fat, and not more than 10 weight-% of crude fibers, and not more than 25 weight-% of ash, and not more than 15 weight-% of water, each based on the total weight of the fish meal, whereby the total amount of all ingredients sums up to 100 weight-%.

More preferably fish meal contains from 50 to 90 weight-% of crude protein and from 5 to 20 weight-% of crude fat, and from 1 to 10 weight-% of crude fibers, and from 5 to 25 weight-% of ash, and from 5 to 15 weight-% of water, each based on the total weight of the fish meal, whereby the total amount of all ingredients sums up to 100 weight-%.

For stabilizing fish meal an amount of at least one compound of formula (I) ranging from 10 to 2000 ppm, preferably ranging from 100 to 1500 ppm, more preferably ranging from 300 to 1000 ppm, based on the total amount of the fish meal, is usually sufficient.

Fish meal is a commercial product made from fish that is used primarily as a protein supplement in compound feed, especially for feeding farmed fish, crustacea, pigs and poultry, and companion animals such as cats and dogs.

A portion of the fish meal is made from the bones and offal left over from processing fish used for human consumption, while the larger percentage is manufactured from wild-caught, small marine fish. It is powder or cake obtained by drying the fish or fish trimmings, often after cooking, and then grinding it. If the fish used is a fatty fish it is first pressed to extract most of the fish oil.

The uses and need of fish meal are increasing due to the rising demand for fish, because fish has the best feed conversion rate of all farmed animals, can be produced well in developing countries and has a small size, i.e. can be slaughtered for preparing a meal, so that there is no need to store the fish. Furthermore, there are no religious constraints concerning the consumption of fish, fish is a source of high quality protein and it is easy to digest.

Fish meal is made by cooking, pressing, drying, and grinding of fish or fish waste to which no other matter has been added. It is a solid product from which most of the water is removed and some or all of the oil is removed. About four or five tons of fish are needed to manufacture one ton of dry fish meal.

Of the several ways of making fish meal from raw fish, the simplest is to let the fish dry out in the sun. This method is still used in some parts of the world where processing plants are not available, but the end-product is of poor quality in comparison with ones made by modern methods.

Currently, all industrial fish meal is usually made by the following process:

Cooking: A commercial cooker is a long, steam-jacketed cylinder through which the fish are moved by a screw conveyor. This is a critical stage in preparing the fishmeal, as incomplete cooking means the liquid from the fish cannot be pressed out satisfactorily and overcooking makes the material too soft for pressing. No drying occurs in the cooking stage.

Pressing: A perforated tube with increasing pressure is used for this process. This stage involves removing some of the oil and water from the material and the solid is known as press cake. The water content in pressing is reduced from 70% to about 50% and oil is reduced to 4%.

Drying: If the fish meal is under-dried, moulds or bacteria may grow. If it is over-dried, scorching may occur and this reduces the nutritional value of the meal.

The two main types of dryers are:

Direct: Very hot air at a temperature of about 500° C. is passed over the material as it is tumbled rapidly in a cylindrical drum. This is the quicker method, but heat damage is much more likely if the process is not carefully controlled.

Indirect: A cylinder containing steam-heated discs is used, which also tumbles the meal.

Grinding: This last step in processing involves the breakdown of any lumps or particles of bone.

The fish meal has to be transported long distances by ship or other vehicles to the various locations, where it is used.

Unmodified fish meal can spontaneously combust from heat generated by oxidation of the polyunsaturated fatty acids in the fish meal. Therefore, it has to be stabilized by antioxidants. Especially advantageous for this purpose are the compounds of formula (I) of the present invention.

Insect Meal

Insect meal has a high content of protein and is therefore, a valuable source of protein.

In general any insect may be manufactured to meal, but insects of special interest in the context of the present invention encompass black soldier flies (*Hermetia* species, commonly called BSF), mealworms (*Tenebrio molitor*), lesser mealworms (*Alphitobius diaperinus*), house cricket (*Acheta domesticus*, grasshoppers (*Locusta migratoria*), buffaloworms (*Alphitobius diaperinus*), cockroaches and domestic flies, whereby black soldier flies (*Hermetia* species, commonly called BSF), mealworms (*Tenebrio molitor*) and lesser mealworms (*Alphitobius diaperinus*) are more preferred.

For stabilizing insect meal an amount of at least one compound of formula (I) ranging from 10 to 1000 ppm, preferably ranging from 30 to 700 ppm, more preferably ranging from 100 to 500 ppm, based on the total amount of the insect meal, is usually sufficient.

II. Feed

The compounds of formula (I) are not only suitable for stabilizing feed ingredients such as poultry meal, fish meal, insect meal and PUFA-containing oil, but also effective antioxidants for feed.

Feed (or 'feedingstuff') means any substance or product, including additives, whether processed, partially processed or unprocessed, intended to be used for oral feeding to animals.

Feed in the context of the present invention is feed for aquatic animals and for terrestrial animals, as well as feed for insects.

For stabilizing feed an amount of at least one compound of formula (I) ranging from 10 to 500 ppm, preferably ranging from 30 to 300 ppm, more preferably ranging from 100 to 250 ppm, based on the total amount of the feed, is usually sufficient.

Further Antioxidants

The compounds of formula (I) can be used in combination with one or more other antioxidants as described below.

In an embodiment of the present invention the feed of the present invention additionally comprises a mixture of 2-tert-butyl-4-methoxyphenol and 3-tert-butyl-4-methoxyphenol, which is known under the name "BHA" (butylated hydroxyanisole).

In a further embodiment of the present invention the feed of the present invention additionally comprises ascorbyl palmitate.

In another embodiment of the present invention the feed of the present invention additionally comprises BHA and ascorbyl palmitate.

Instead of ascorbyl palmitate other esters of ascorbic acid such as the esters of ascorbic acid with linear $C_{12-20}$ alkanols, preferably the esters of ascorbic acid with linear $C_{14-18}$ alkanols, may also be used, so that further embodiments of the present invention are directed to feed that additionally comprises esters of ascorbic acid with linear $C_{12-20}$ alkanols, preferably esters of ascorbic acid with linear $C_{14-18}$ alkanols, more preferably ascorbyl palmitate, whereby optionally BHA may also be present.

The feed may also comprise additionally alpha-tocopherol and/or gamma-tocopherol, whereby either an ester of ascorbic acid with a linear $C_{12-20}$ alkanol with the preferences as given above or BHA or both may additionally be present.

The feed itself is described in more detail below.

Feed for Poultry

The feed for poultry differs from region to region. In the following Tables V and VI typical examples for diets in Europe and Latin America are given. These diets include cereals such as wheat, rye, maize/corn, minerals such as NaCl, vegetable oils such as soya oil, amino acids and proteins.

TABLE V

European diet

| Ingredients (%) | Starter Period (day 0-21) | Grower Period (day 22-36) |
|---|---|---|
| Wheat | 20.00 | 22.50 |
| Rye | 12.00 | 12.00 |
| Soybean meal | 34.00 | 28.50 |
| Maize | 27.00 | 28.50 |
| Vegetable Oil | 3.10 | 4.20 |
| NaCl | 0.10 | 0.10 |
| DL Methionine | 0.24 | 0.24 |
| L-Lysine | 0.15 | 0.15 |
| Limestone | 0.85 | 0.85 |
| Dicalcium Phosphate | 1.50 | 1.90 |
| Vitamin & Mineral mix | 1.00 | 1.00 |
| Coccidiostat (Avatec) | 0.06 | 0.06 |
| $TiO_2$ | — | 0.10 |
| calculated Provision | | |
| apparent metabolizable energy, MJ/kg | 12.5 | 12.90 |
| apparent metabolizable energy, kcal/kg | 2986 | 3082 |
| crude Protein, % | 21.2 | 19.1 |
| Methionine + Cysteine, % | 0.89 | 0.83 |
| Lysine, % | 1.23 | 1.09 |
| Calcium, % | 0.83 | 0.91 |
| total phosphorus, % | 0.68 | 0.73 |
| available phosphorus, % | 0.35 | 0.40 |

TABLE VI

Latin American diet

| Ingredients (%) | Starter | Grower |
|---|---|---|
| Corn | 53.0 | 57.1 |
| Soybean meal | 38.5 | 34.2 |
| Calcium | 0.70 | 0.70 |
| Phosphorus | 2.40 | 2.00 |
| NaHCO$_3$ | 0.23 | 0.24 |
| NaCl | 0.20 | 0.20 |
| Methionine | 0.30 | 0.10 |
| Lysine | 0.21 | 0.00 |
| Soya Oil | 3.50 | 4.50 |
| Premix | 1.00 | 1.00 |
| Calculated provision (%) | | |
| Crude protein | 22.4 | 20.4 |
| apparent metabolizable energy, (MJ/kg) | 12.7 | 13.2 |
| apparent metabolizable energy, (kcal/kg) | 3034 | 3154 |
| Total phosphorus | 0.86 | 0.76 |
| Calcium | 1.00 | 0.85 |
| Available phosphorus | 0.44 | 0.38 |
| d-Lysine | 1.25 | 0.98 |
| d-Methionine + Cysteine | 0.91 | 0.68 |
| d-Threonine | 0.77 | 0.71 |
| Na | 0.18 | 0.18 |
| Cl | 0.20 | 0.19 |

Pet Food

Pet foods are formulated to meet nutrient specifications using combinations of multiple ingredients to meet the targeted nutrient specification.

Poultry meal e.g. is an ingredient that is commonly found in Dog and Cat foods.

The nutrient specifications for a complete and balanced dog or cat food will meet or exceed the guidelines provided by AAFCO (American Association of Feed Control Officials). The ingredient composition of pet-food can include any legal feed ingredient so number of combinations are not quite infinite but close. Some examples of ingredient used in dog and cat foods can be found in Table VII below:

TABLE VII

| Ingredient Class/Ingredient | Use rates |
|---|---|
| 1 ANIMAL MEALS | 10-35% |
| Chicken | |
| Turkey | |
| Duck | |
| Poultry Br-Product | |
| Lamb | |
| Venison | |
| Beef | |
| Pork | |
| Meat & Bone | |
| Fish | |
| 2 FRESH MEATS | 3-20% |
| Chicken | |
| Turkey | |
| Duck | |
| Lamb | |
| Venison | |
| Beef | |
| Pork | |
| Fish | |
| 3 VEGETABLE PROTEINS | 8-20% |
| Soybean Meal | |
| Corn Gluten Meal | |
| Pea Protein | |
| Potato Protein | |
| Soy Protein Conc/Isolates | |
| 4 GRAINS | 0-70% |
| Corn/Maize | |
| Wheat | |
| Brown Rice/Brewers Rice | |
| Oatmeal/Oat Groats | |
| Barley | |
| Millet | |
| Milo/Sorghum | |
| Rye | |
| Corn Gluten Feed | |
| Wheat Middlings | |
| 5 FIBER SOURCES | 2-8% |
| Beet Pulp | |
| Corn Bran | |
| Wheat Bran | |
| Cellulose | |
| Tomato Ponace | |
| Potato Fiber | |
| Pea Fiber | |
| 6 FATS & OILS | 1-15% |
| Animal Fat | |
| Poultry Fat | |
| Chicken Fat | |
| Beef Tallow | |
| Sunflower Oil | |
| Canola Oil | |
| 7 MICRONUTRIENTS | 0.10-1% |
| Vitamins | |
| Minerals | |
| Others (e.g. Fructooligosaccharides (FOS) used as a pre-biotic) | |
| 8 PALATANTS (FLAVORS) | 0-5% |
| 9 Other non-basic ingredients | |
| Dried Egg Product | 1-15% |
| Fish Oil | 0.5-2% |
| Fish Meal | 1-4% |
| Flaxseed | 1-4% |
| Dried Peas | 5-30% |
| Dried Chickpeas | 5-30% |
| Dried Lentils | 5-10% |
| Dried Potatoes | 5-20% |
| Dried Sweet Potatoes | 5-20% |
| Tapioca Starch | 5-15% |
| Potato Starch | 5-15% |
| Pea Starch | 5-15% |

For stabilizing pet food an amount of at least one compound of formula (I) ranging from 10 to 500 ppm, preferably ranging from 30 to 300 ppm, more preferably ranging from 100 to 250 ppm, based on the total amount of the pet food, is usually sufficient.

Feed for Fish

A typical example of feed for fish comprises the following ingredients, whereby all amounts are given in weight-%, based on the total weight of the feed for fish:

Fish meal in an amount ranging from 5 to 15 weight-%, preferably fish meal in said amount comprising the compounds of formula (I) of the present invention;

fish hydrolysates in an amount ranging from 0 to 5 weight-%;

vegetable proteins in an amount ranging from 30 to 45 weight-%;

binders, mainly starch, in an amount ranging from 9 to 12 weight-%;

micro-ingredients such as vitamins, choline, minerals, mono calcium phosphate ("MCP") and/or amino acids in an amount ranging from 3 to 6 weight-%;

marine oil in an amount ranging from 5 to 10 weight-%, preferably marine oil in said amount comprising the compounds of formula (I) of the present invention;

vegetable oil in an amount ranging from 20 to 25 weight-%, preferably vegetable oil in said amount comprising the compounds of formula (I) of the present invention; and whereby the amount of all ingredients sum up to 100 weight-%.

For stabilizing feed for fish an amount of at least one compound of formula (I) ranging from 10 to 1000 ppm, preferably ranging from 30 to 700 ppm, more preferably ranging from 100 to 500 ppm, based on the total amount of the feed for fish, is usually sufficient.

Manufacturing Process According to the Present Invention

In the context of the present invention an advantageous process for the manufacture of compounds of formula (IA) has also been found. Thus, the present invention is also directed to a process for the manufacture of a compound of formula (IA),

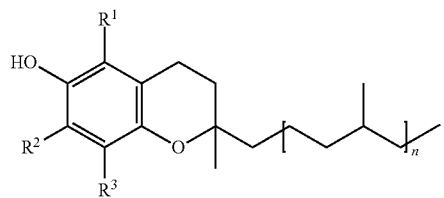

(IA)

comprising the step of reacting a compound of formula (II) with a compound of formula (III) in the presence of an acid catalyst and in a mixture of two solvents,

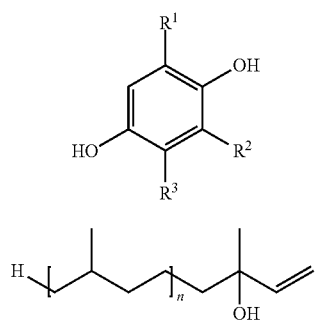

(II)

(III)

wherein n is 3, and
$R^1$ and $R^3$ are independently from each other H or methyl, and $R^2$ is either H or methyl or methoxy, and
the first of the two solvents is selected from ethylene carbonate, propylene carbonate, 1,2-butylene carbonate, gamma-butyrolactone and water, and the second of the two solvents is selected from hexane, cyclohexane, heptane, ortho-xylene, meta-xylene, para-xylene, mesitylene, pseudocumene, methyl tert-butyl ether, and toluene.

The process is now described in more detail below.

Solvent Mixture

Preferably the first of the two solvents is ethylene carbonate or propylene carbonate, and the second of the two solvents is selected from either hexane, cyclohexane or heptane. More preferably the first of the two solvents is ethylene carbonate and the second of the two solvents is heptane.

The term "hexane" encompasses n-hexane, as well as any mixture of the isomers of hexane. The same applies for heptane.

Preferably the volume ratio of the first solvent to the second solvent during the reaction is in the range of 1:4 to 4:1, more preferably the volume ratio of the first solvent to the second solvent is in the range of 1:3 to 3:1 most preferably the volume ratio of the first solvent to the second solvent is in the range of 1:2 to 2:1.

Preferably the total amount of the two solvents is in the range of 1 to 10 kg, more preferably in the range of 2 to 7 kg, most preferably in the range of 2.5 to 6 kg, per kg of the compound of formula (II).

In an embodiment of the process of the present invention all embodiments with regard to the solvent mixture and the preferences as given above are realized.

Catalyst

The acid catalyst is preferably selected from Brønsted acids, Lewis acids and any mixtures thereof.

Examples of preferred Brønsted acids are sulfuric acid, phosphoric acid, acidic ion-exchange resins, acidic clays, zeolites, hydrochloric acid, trifluoroacetic acid, trichloroacetic acid, acetic acid, formic acid, methanesulfonic acid, benzenesulfonic acid, para-toluenesulfonic acid, ethanesulfonic acid, trifluoromethanesulfonic acid, bis(perfluoroalkyl-sulfonyl)methanes $(R'SO_2)(R''SO_2)CH_2$ wherein R' and R'' each signify independently from each other a perfluoroalkyl group of the formula $C_nF_{2n+1}$ where n is an integer from 1 to 10, tris(perfluorosulfonyl)methanes $(R'SO_2)(R''SO_2)(R'''SO_2)CH$, wherein R', R'' and R''' each signify independently from each other a perfluoroalkyl group of the formula $C_nF_{2n+1}$ where n is an integer from 1 to 10, and whereby at least two of R', R'' and R''' are identical perfluoroalkyl groups, or R' signifies the pentafluorophenyl group ($—C_6F_5$) and R'' and R''' each signify an identical perfluoroalkyl group of the above formula $C_nF_{2n+1}$, methanetrisulfonic acid, and bis(trifluormethylsulfonyl)imide, and any mixture thereof, whereby the use of single catalysts is preferred.

Examples of preferred Lewis acids are $Al(OTf)_3$, $Sc(OTf)_3$, $Sc(NTf_2)_3$, $ScCl_3$, $Yb(OTf)_3$, $YbCl_3$, $Cu(OTf)_2$, $FeCl_2$, $Fe(OTf)_2$, $ZnCl_2$, $Zn(OTf)_2$, $Zn(NTf_2)_3$, $YCl_3$, $Y(OTf)_3$, $InCl_3$, $InBr_3$, $In(OTf)_3$, $In(NTf_2)_3$, $La(OTf)_3$, $Ce(OTf)_3$, $Sm(OTf)_3$, $Gd(OTf)_3$ and $Bi(OTf)_3$ in the presence or absence of 2,2-bipyridine and any mixture thereof, whereby the use of single catalysts is preferred.

Preferably the acid catalyst is para-toluenesulfonic acid, sulfuric acid, methanesulfonic acid, $Al(OTf)_3$, $Sc(OTf)_3$, or $In(OTf)_3$, most preferably the acid catalyst is para-toluenesulfonic acid or $Al(OTf)_3$.

Preferably the amount of the acid catalyst is in the range of 0.001 to 5 mol equivalents, more preferably in the range of 0.005 to 1 mol equivalents, most preferably in the range of 0.01 to 0.1 mol equivalents, relative to the amount of compound of formula (III).

Preferably the molar ratio of the compound of formula (II) to the compound of formula (III) is in the range of 6.0:1 to 1.1:1, more preferably it is in the range of 4.0:1 to 1.2:1, even more preferably it is in the range of from 3.0:1 to 1.3:1, most preferably it is in the range of 2.0:1 to 1.5:1.

In an embodiment of the process of the present invention all embodiments with regard to the acid catalyst and the preferences as given above are realized.

Reaction Conditions

The reaction is preferably carried out at a temperature in the range of 70 to 160° C., more preferably in the range of 80 to 130° C., most preferably in the range of 90-105° C.

The reaction is preferably carried out at a pressure in the range of 0.8 to 20 bar (absolute), more preferably at a pressure in the range of 0.8 to 10 bar (absolute), most preferably at a pressure in the range of 0.8 to 5 bar (absolute).

An advantage of the process according to the present invention is that the acid catalyst is reusable.

In an embodiment of the process of the present invention all embodiments with regard to the reaction conditions and the preferences as given above are realized.

In further embodiments of the process of the present invention the preferred embodiments with respect to the starting material, the catalyst, the solvent mixture and the reaction conditions are partly or all realized.

The invention is now further illustrated in the following non-limiting examples.

EXAMPLES

R,R,R-delta-tocopherol (compound of formula (1A)) is commercially available, e.g. from Sigma-Aldrich, Product no. T2028, (+)-d-tocopherol, >90%.

Figure 2:
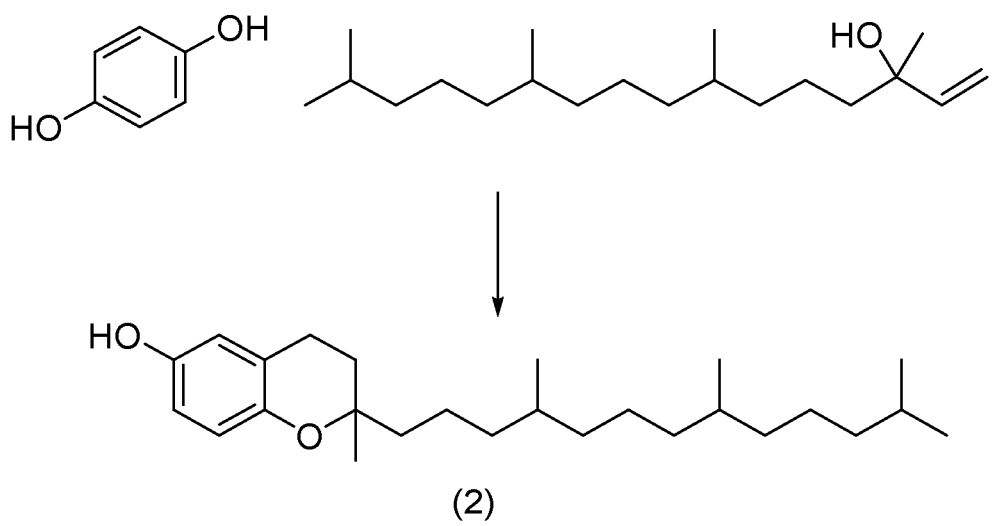
FIG. 2 shows the synthesis of the compoun of formula (2) (2-methyl-2-(4,8,12-trimethyltridecyl) Chroman-6-ol=tocol) according to Example 1 below.

Example 1: Synthesis of the Compound of Formula (2) (2-methyl-2-(4,8,12-trimethyltridecyl)chroman-6-ol=tocol) (see FIG. 2)

A 200 mL 4-necked flask equipped with magnetic stirrer, oil bath, thermometer and argon supply was charged with 1,4-hydroquinone (12.0 g, 109 mmol, 99.8%, 4.0 mol equiv.), isophytol (8.06 g, 25.8 mmol, 95.1%, 1.0 mol equiv.), ethylene carbonate (50 mL) and heptane (50 mL) forming a 2-phase system. Then, para-toluenesulfonic acid monohydrate (0.10 g, 0.52 mmol, 2 mol %) was added and the mixture was heated to reflux. After 80 min, the reaction mixture was cooled to 50° C. and the phases were separated. The lower ethylene carbonate phase was extracted with heptane (25 mL). The combined organic phases were extracted with water (25 mL), dried over sodium sulfate and concentrated in vacuo (40° C./50-20 mbar). The residue was purified by column chromatography, eluent gradient heptane/EtOAc 95:5 to 85:15 (w/w). The combined pure fractions were concentrated in vacuo (40° C./200-10 mbar) and dried under high vacuum at 40° C., furnishing tocol as light beige oil (6.81 g, 96% purity by quant. NMR, 16.8 mmol, 65% yield).

GC-HRMS: 99.2 area %. Calcd. for $C_{26}H_{44}O_2$ (M$^+$) 388.3341, found 388.3344.

$^1$H NMR (300 MHz, CHLOROFORM-d) δ 0.82-0.91 (m, 12H), 1.00-1.45 (m, 18H), superimposed by 1.26 (s, 3H), 1.46-1.67 (m, 3H), 1.68-1.88 (m, 2H), 2.71 (t, J=6.8 Hz, 2H), 4.26 (br s, 1H, OH), 6.52-6.63 (m, 2H), 6.66 (d, J=8.5 Hz, 1H) ppm.

$^{13}$C NMR (75 MHz, CHLOROFORM-d) δ 19.58, 19.62, 19.63, 19.66, 19.73, 21.07, 22.26, 22.61, 22.70, 24.03, 24.42, 24.78, 26.39, 27.93, 30.82, 30.85, 32.65, 32.67, 32.73, 35.39, 37.25, 37.36, 37.41, 37.46, 37.55, 39.34, 39.76, 39.80, 76.10, 114.62, 115.57, 117.74, 121.97, 147.59, 148.39 ppm.

Comparison Example: Reaction Carried Out in One Solvent Only

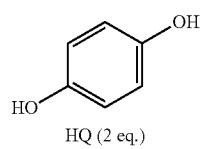

HQ (2 eq.)

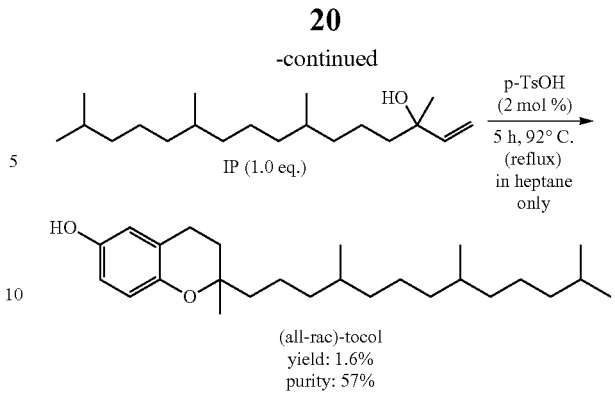

(all-rac)-tocol
yield: 1.6%
purity: 57%

"eq."=mol equivalent(s); h=hours; p-TsOH=para-toluenesulfonic acid.

Example 2: Antioxidant Activities in Pet Food, Poultry Meal and Fish Meal

Compound of formulae (1A) was tested in pet food, poultry meal and/or fish meal and its corresponding antioxidant efficacy values ("EV") determined subsequently.

Determination of the Antioxidant Efficacy Value "EV"

Oxidative stability was assessed using an Oxipres (Mikrolab Aarhus A/S, Hojbjerg, Denmark). The ML OXIPRES® is designed to monitor the oxidation of heterogeneous products. Consumption of oxygen results in a pressure drop which is measured by means of pressure transducers. The samples are heated to accelerate the process and shorten the analysis time (Mikrolab Aarhus 2012).

Sample weights were 50 g. They were loaded into the Oxipres vessels and placed inside the stainless-steel pressure vessel and sealed. The pressure vessels were purged with pure oxygen and filled to an initial oxygen pressure of 5 bar and maintained at 70° C. during measurement (D. Ying, L. Edin, L. Cheng, L. Sanguansri, M. A. Augustin, *LWT—Food Science and Technology* 2015, 62, 1105-1111: "Enhanced oxidative stability of extruded product containing polyunsaturated oils.").

The oxygen pressure was recorded as function of time. After sample load and temperature rise the pressure in the device is increasing within 10 hours. Thereafter it is decreasing. Consequently, the starting pressure is considered as being the pressure that is achieved after 10 hours. The analysis ends after 130 hours at 70° C. The oxygen consumption 'O$_2$' of the tested sample is calculated as follows:

$$\text{O2 consumption (as \%)} = 1 - \left[\frac{\text{Pressure after 130 hours in } \textit{Oxipres}}{\text{Pressure after 10 hours in } \textit{Oxipres}}\right]$$

TABLE 1

Oxipres performance of the three matrices

|  | Matrix 1<br>Pet food | Matrix 2<br>Poultry meal | Matrix 3<br>Fish meal |
|---|---|---|---|
| Oxipres results - O$_2$ consumption | 25% | 32% | 31% |
| CV (= coefficient of variation) | 19% | 13% | 9% |

A factor of protection called 'EV' (Efficacy Value) was developed to quantify with a relative number (relative to BHT) the antioxidant effect of the tested candidates. EV was calculated as follows:

$$EV_{AOX\ candidate} = \frac{1}{(O2\ consumption_{AOX\ candidate} / O2\ consumption_{BHT})}$$

EV, being relative to BHT (3,5-di-tert-butyl-4-hydroxytoluene) (EV=1), makes it possible to compare the antioxidant compounds in a defined feed application. Here pet food, poultry meal and fish meal have been used as feed application with the composition as given in the following table 2.

TABLE 2

| Parameters analyzed | Amount | Pet food Matrix 1 | Poultry meal Matrix 2 | Fish meal Matrix 3 |
|---|---|---|---|---|
| Crude Protein | g/100 g | 24 | 56 | 68 |
| Total fat | g/100 g | 9.8 | 19.4 | 12.4 |
| Saturated fatty acids | g/100 g Fat | 32.8 | 30.8 | 20.5 |
| Mono unsaturated fatty acids | g/100 g Fat | 38.1 | 43.5 | 31.0 |
| Poly unsaturated fatty acids | g/100 g Fat | 19.6 | 17.9 | 28.3 |
| Omega 3 | g/100 g Fat | 3.76 | 0.72 | 25.9 |
| Omega 6 | g/100 g Fat | 15.8 | 17.1 | 2.36 |
| Saturated fatty acids | g/100 g | 3.21 | 5.97 | 2.55 |
| Mono unsaturated fatty acids | g/100 g | 3.73 | 8.42 | 3.85 |
| Poly unsaturated fatty acids | g/100 g | 1.91 | 3.45 | 3.50 |
| Omega 3 | g/100 g | 0.367 | 0.139 | 3.22 |
| Omega 6 | g/100 g | 1.55 | 3.32 | 0.294 |
| Omega 3 + 6 | g/100 g | 1.92 | 3.46 | 3.51 |
| Unsaturated Fatty acids | g/100 g | 7.56 | 15.33 | 10.86 |
| Moisture content | % | 8.0 | 4.8 | 7.3 |
| water activity | | 0.49 | 0.42 | 0.53 |
| pH | | 7.8 | 7.6 | 7.4 |

The EV of BHT is 1.0 in all three matrices, the EVs of alpha-tocopherol are shown in Table 3 below. An efficacy value 0.6 is considered as acceptable, an efficacy value equal or greater to the one of alpha-tocopherol as good, and an efficacy value equal or greater to the one of BHT as very good.

TABLE 3

| Compound | BHT | Alpha-tocopherol |
|---|---|---|
| EV in pet food (matrix 1) | 1.0 | 0.77 |
| EV in poultry meal (matrix 2) | 1.0 | 0.74 |
| EV in fish meal (matrix 3) | 1.0 | 0.88 |

Compound of formula (1A) was mixed into each matrix 1, 2 or 3 (pet food, poultry meal, fish meal) in an equimolar ratio compared to BHT. Batches of 200 g feed were produced in order to handle a minimum of 30 mg of antioxidant. First, a 1% pre-dilution of the antioxidant with the feed material was made. Then this pre-dilution was added to the final batch, mixed, sieved (1.25 mm sieve) and mixed using a Turbula® mixer. Thereafter 55 g of the final batch were packed into polyethylene bags, and stored at 4° C. until start of the Oxipres assay. Spare sample were stored at 4° C.

Results obtained from pet food samples (matrix 1) are shown in the following Table 4. Compound of formula (1A) showed a higher efficacy value than alpha-tocopherol (EV=0.77) and a higher efficacy value than BHT (EV=1.0) in pet food.

TABLE 4

| Compound | of formula (1A) (R,R,R-delta-tocopherol) | BHT | alpha-tocopherol |
|---|---|---|---|
| EV in pet food (matrix 1) | 1.07 | 1.0 | 0.77 |

Results obtained from poultry meal samples (matrix 2) are shown in the following Table 5. Compound of formula (1A) showed a higher efficacy value than alpha-tocopherol (EV=0.74) and a higher efficacy value than BHT (EV=1.0) in poultry meal.

TABLE 5

| Compound | of formula (1A) (R,R,R-delta-tocopherol) | BHT | alpha-tocopherol |
|---|---|---|---|
| EV in poultry meal (matrix 2) | 1.08 | 1.0 | 0.74 |

Results obtained from fish meal samples (matrix 3) are shown in the following Table 6. Compound of formula (1A) showed a higher efficacy value than alpha-tocopherol (EV=0.88) and a higher efficacy value than BHT (EV=1) in fish meal.

TABLE 6

| Compound | of formula (1A) (R,R,R-delta-tocopherol) | BHT | alpha-tocopherol |
|---|---|---|---|
| EV in fish meal (matrix 3) | 1.12 | 1.0 | 0.88 |

Example 3: Antioxidant Activities of Compound of Formula (2) in Fish Oil and Algal Oil Compound of formula (2) was tested in fish oil and algal oil. The blank oil, i.e. oil without any antioxidant, and oil containing "MNT" have been used as benchmark. Any compound better in antioxidant activity than the blank oil indicates that it has antioxidant activity. The comparison with MNT gives an indication about the amount of the antioxidant effect, relative to the activity of MNT.

"MNT" consists of mixed natural tocopherols and is commercially available e.g. as "Tocomix 70 IP" from AOM (Buenos Aires, Argentina). Tocomix 70 IP comprises d-alpha-tocopherol, d-beta-tocopherols, d-gamma-tocopherols and d-delta-tocopherol, whereby the total amount of tocopherols is at least 70.0 weight-% and the amount of non-alpha tocopherols is at least 56.0 weight-%.

Materials and Methods

Compound of formula (2) was used in both fish and algal oils to see its antioxidant effect in these oils. Antioxidant effect was determined using mainly the Oil Stability Index (OSI). A storage stability study was performed to compare the variation of primary oxidation products, the hydroperoxides, generated during oxidation, measured in terms of peroxide value (PV) and the secondary oxidation products which were measured and determined as anisidine reactive substances or p-anisidine value (p-AV) of oil samples containing this compound.

Oxidative Stability

Two concentration levels were used. Compound of formula (2) was added in the concentrations of 0.5 mg/g (low level) and 2 mg/g (high level) to 5 g of oil and used in the Oxidative Stability Instrument operated at 80° C. with the continuous air flow rate at −40 psi. All samples were run in duplicate. The Protection Factors (PF) for compound of formula (2) in oil were calculated in percentage as:

$$PF\ (\%) = \frac{100\% \times (OSI \text{ of the sample with antioxidant} - OSI \text{ of the sample without antioxidant})}{OSI \text{ of the sample without antioxidant}}$$

Storage Stability

Two different concentrations of compound of formula (2) were used for the storage stability study. Compound of formula (2) and MNT were added, each individually, to 40 g of fish oil samples in 60 ml amber bottles at 0.5 mg/g and 2 mg/g levels, thoroughly mixed and stored at ambient temperature storage for 19 days. All sample bottles were stored open to air, away from light. Compound of formula (2) was soluble in oil. Peroxide values (PV) and p-anisidine values (p-AV) were determined at different times for 19 days.

Results

OSI values of the fish oil samples containing compound of formula (2), in comparison to the same levels of MNT, are shown in Table 7 and 8.

TABLE 7

Oil Stability Indices (OSI) of FG30TG fish oil stabilized with compound of formula (2) (SD = standard deviation)

| | OSI (h) | SD |
|---|---|---|
| Blank (FG30TG) | 5.00 | 0.1 |
| 0.5 mg/g of MNT | 5.88 | 0.0 |
| 2 mg/g of MNT | 6.53 | 0.5 |
| 0.5 mg/g of compound of formula (2) | 5.68 | 0.2 |
| 2 mg/g of compound of formula (2) | 7.75 | 0.1 |

TABLE 8

Protection Factors (PF) of compound of formula (2) in fish oil (80° C.)

| | PF [%] |
|---|---|
| 0.5 mg/g of MNT | 17.5 |
| 0.5 mg/g of compound of formula (2) | 13.5 |
| 2 mg/g of MNT | 30.5 |
| 2 mg/g of compound of formula (2) | 55 |

Based on the Oil Stability Index data, the compound of formula (2) showed higher OSI values than MNT in fish oil.

OSI values and Protection Factors (PF) of the algal oil samples containing compound of formula (2), in comparison to the same levels of MNT, are shown in Table 9 and 10.

TABLE 9

Oxidative stability of crude algal oil stabilized with compound of formula (2) (SD = standard deviation)

| | OSI (h) | SD |
|---|---|---|
| Blank (Crude algal oil) | 15.00 | 0.6 |
| 0.5 mg/g of MNT | 15.70 | 0.8 |
| 2 mg/g of MNT | 15.70 | 0.0 |
| 0.5 mg/g of compound of formula (2) | 15.98 | 0.3 |
| 2 mg/g of compound of formula (2) | 17.10 | 0.1 |

TABLE 10

Protection Factors (PF) of compound of formula (2) in crude algal oil (80° C.)

| | PF [%] |
|---|---|
| 0.5 mg/g of MNT | 4.7 |
| 0.5 mg/g of compound of formula (2) | 6.5 |
| 2 mg/g of MNT | 4.8 |
| 2 mg/g of compound of formula (2) | 14 |

Based on the Oil Stability Index data, the compound of formula (2) showed also higher OSI values than MNT in algal oil.

Peroxide values of fish oil samples at low (0.5 mg/g) and high levels (2 mg/g) are shown in Tables 11 and 12 respectively.

TABLE 11

Peroxide values (PV, meq/kg) during storage at 25° C. (0.5 mg/g level)

| | Initial | 1 day | 5 days | 8 days | 14 days | 19 days |
|---|---|---|---|---|---|---|
| Blank | 1 | 1.1 | 2.3 | 7.7 | 13.2 | 19.1 |
| 0.5 mg/g of MNT | 1 | 1 | 2.3 | 7 | 13.6 | 22.9 |
| 0.5 mg/g of compound of formula (2) | 1 | 1.1 | 2.3 | 8 | 14 | 23.7 |

TABLE 12

Peroxide values (PV, meq/kg) during storage at 25° C. (2 mg/g level)

| | Initial | 1 day | 5 days | 8 days | 14 days | 19 days |
|---|---|---|---|---|---|---|
| Blank | 1 | 1.1 | 2.3 | 7.7 | 13.2 | 19.1 |
| 2 mg/g of MNT | 1 | 0.9 | 1.6 | 2.9 | 6.1 | 18.3 |
| 2 mg/g of compound of formula (2) | 1 | 0.9 | 2.4 | 3.7 | 6.6 | 16.2 |

With regard to primary oxidation products (hydroperoxides) generated in the fish oil samples containing compound of formula (2) or MNT, determined as peroxide values (PV), the samples did not show a considerable difference at both concentration levels used although the untreated oil produced higher peroxide values than those containing compound of formula (2) or MNT, most of the times.

The p-AV of the same samples at low (0.5 mg/g) and high levels (2 mg/g) are shown in Tables 13 and 14 respectively.

TABLE 13 p-Anisidine value (p-AV) during storage at 25° C. (0.5 mg/g level)

| | Initial | 1 day | 5 days | 8 days | 14 days | 19 days |
|---|---|---|---|---|---|---|
| Blank | 9.4 | 9.5 | 9.4 | 11.3 | 12.7 | 14.3 |
| 0.5 mg/g of MNT | 9.4 | 9.5 | 9.3 | 11.7 | 13 | 15.8 |
| 0.5 mg/g of compound of formula (2) | 9.4 | 9.5 | 9.4 | 11.8 | 13.4 | 14.7 |

TABLE 14 p-Anisidine value (p-AV) during storage at 25° C. (2 mg/g level)

| | Initial | 1 day | 5 days | 8 days | 14 days | 19 days |
|---|---|---|---|---|---|---|
| Blank | 9.4 | 9.5 | 9.4 | 11.3 | 12.7 | 14.3 |
| 2 mg/g of MNT | 9.4 | 9.4 | 9.2 | 10.2 | 10 | 9.9 |
| 2 mg/g of compound of formula (2) | 9.4 | 9.5 | 9.3 | 10.4 | 10.4 | 11.2 |

Also, there was no considerable difference in the variation of p-anisidine values (p-AV) in all these samples except the sample which did not contain any antioxidants ("untreated sample"). The untreated sample had relatively higher p-AV values than all other samples showing that compound of formula (2) has antioxidant properties.

The invention claimed is:

1. A method to stabilize a feed against oxidation which comprises incorporating into the feed an oxidation stabilizing effective amount of an antioxidant compound according to formula (I):

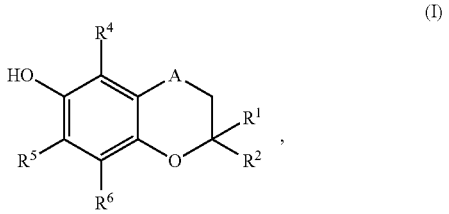

wherein
one of the two substituents $R^1$ and $R^2$ is $C_{12-21}$-alkyl and the other of the two substituents $R^1$ and $R^2$ is either hydrogen or $C_{1-5}$-alkyl or $(CH_2)_n$—OH with n being an integer from 1 to 5,
A is $CH(R^3)$,
$R^3$, $R^4$ and $R^6$ are independently from each other H or $C_{1-4}$-alkyl, and
$R^5$ is H, OH, $C_{1-4}$-alkyl or $C_{1-4}$-alkoxy;
with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl.

2. The method according to claim 1, wherein $R^1$ and $R^2$ is $C_{12-21}$-alkyl and the other of the two substituents $R^1$ and $R^2$ is either hydrogen or $C_{1-5}$-alkyl, $R^3$, $R^4$ and $R^6$ are independently from each other H or $C_{1-4}$-alkyl, and
$R^5$ is H, OH, $C_{1-4}$-alkyl or $C_{1-4}$-alkoxy.

3. The method according to claim 1, wherein the compound of formula (I) is compound of formula (1), a compound of formula (2) or any mixture thereof:

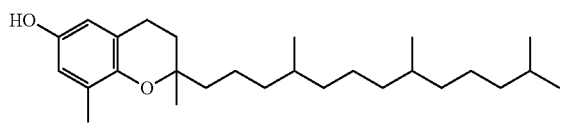

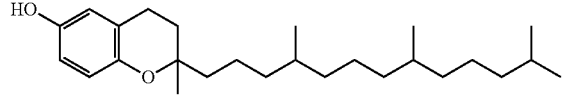

4. The method according to claim 1, wherein the method comprising incorporating the antioxidant compound of formula (I) into a feed additive selected from the group consisting of poultry meal, fish meal, insect meal and PUFA-containing oil, and thereafter incorporating the feed additive into the feed.

5. The method according to claim 1, wherein the feed is selected from the group consisting of feed for aquatic animals, feed for terrestrial animals and feed for insects.

6. The method according to claim 4, wherein the PUFA-containing oil is selected from the group consisting of marine oils, microbial oils, fungal oils and algal oils.

7. The method according to claim 1, wherein
one of the two substituents $R^1$ and $R^2$ is $C_{12-21}$-alkyl and the other of the two substituents $R^1$ and $R^2$ is either hydrogen, methyl or ethyl,
$R^3$ and $R^4$ are independently from each other H or methyl or ethyl,
$R^5$ is H, OH, methyl, ethyl, methoxy or ethoxy; and
$R^6$ is H or $C_{1-4}$-alkyl,
with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl.

8. The method according to claim 7, wherein $R^6$ is H, methyl or ethyl.

9. The method according to claim 1, wherein
one of the two substituents $R^1$ and $R^2$ is $C_{12-21}$-alkyl and the other of the two substituents $R^1$ and $R^2$ is either hydrogen or methyl,
$R^3$ is H,
$R^4$ is H or methyl, and
$R^6$ is H or $C_{1-4}$-alkyl.

10. The method according to claim 7, wherein
$R^5$ is H, OH, methyl or methoxy, and
$R^6$ is H, methyl or ethyl,
with the proviso that at least two of $R^4$, $R^5$ and $R^6$ are not methyl, when $R^3$ is H and one of the substituents $R^1$ and $R^2$ is methyl and the other of the two substituents $R^1$ and $R^2$ is $C_{12-21}$-alkyl.

11. The method according to claim 1, wherein the antioxidant compound of formula (I) is present in the feed in an amount of 10 to 500 ppm.

12. The method according to claim 4, wherein the feed additive is a marine oil and wherein the antioxidant compound of formula (I) is incorporated into the feed additive in an amount of 10 to 500 ppm.

13. The method according to claim 4, wherein the feed additive is a poultry meal and wherein the antioxidant compound of formula (I) is incorporated into the feed additive in an amount of 10 to 1000 ppm.

14. The method according to claim 4, wherein the feed additive is a fish meal and wherein the antioxidant compound of formula (I) is incorporated into the feed additive in an amount of 10 to 2000 ppm.

15. The method according to claim 4, wherein the feed additive is an insect meal and wherein the antioxidant compound of formula (I) is incorporated into the feed additive in an amount of 10 to 1000 ppm.

16. The method according to claim 1, wherein the feed is selected from the group consisting of feed for poultry, feed for pets and feed for pigs.

\* \* \* \* \*